US008414535B2

(12) United States Patent  
Jacobsen et al.

(10) Patent No.: US 8,414,535 B2  
(45) Date of Patent: Apr. 9, 2013

(54) MINIATURE PUMP DEVICE AND METHOD

(75) Inventors: Stephen C. Jacobsen, Salt Lake City, UT (US); Shane Olsen, Centerville, UT (US)

(73) Assignee: Sterling Investments LC, Salt Lake City, UT (US)

( * ) Notice: Subject to any disclaimer, the term of this patent is extended or adjusted under 35 U.S.C. 154(b) by 391 days.

(21) Appl. No.: 12/082,676

(22) Filed: Apr. 11, 2008

(65) Prior Publication Data  
US 2008/0262429 A1 Oct. 23, 2008

Related U.S. Application Data

(60) Provisional application No. 60/923,334, filed on Apr. 12, 2007.

(51) Int. Cl.  
*A61M 1/00* (2006.01)  
*F04B 17/00* (2006.01)  
*F01B 9/00* (2006.01)

(52) U.S. Cl. .......................... 604/151; 417/415; 92/140

(58) Field of Classification Search .................... 604/45, 604/122, 141, 144, 146, 151, 156  
See application file for complete search history.

(56) References Cited

U.S. PATENT DOCUMENTS

| 2,881,749 A | 4/1959 | Pringham |
| 3,245,426 A | 4/1966 | Kreuter et al. |
| 3,390,919 A | 7/1968 | Boyce |
| 3,650,093 A * | 3/1972 | Rosenberg ............................ 96/6 |
| 3,712,579 A | 1/1973 | Murray et al. |
| 4,373,527 A | 2/1983 | Fischell |
| 5,485,984 A | 1/1996 | Itoi et al. |
| 5,607,418 A | 3/1997 | Arzbaecher |
| 5,694,919 A | 12/1997 | Rubsamen et al. |
| 6,656,159 B2 * | 12/2003 | Flaherty ......................... 604/131 |
| 6,669,663 B1 | 12/2003 | Thompson |
| 6,726,672 B1 | 4/2004 | Hanly et al. |
| 7,264,611 B2 | 9/2007 | Christenson et al. |
| 7,367,968 B2 | 5/2008 | Rosenberg et al. |
| 7,429,255 B2 | 9/2008 | Thompson |
| 2003/0121414 A1* | 7/2003 | Cautenet et al. ................. 92/140 |
| 2003/0163089 A1* | 8/2003 | Bynum .......................... 604/154 |
| 2003/0229330 A1 | 12/2003 | Hickle |
| 2004/0249334 A1 | 12/2004 | Cull |
| 2010/0135831 A1 | 6/2010 | Jacobsen et al. |

OTHER PUBLICATIONS www.instechlabs.com, Instech Solomon, Pumps, Pegasus Infusion Pump, 2 pages.  
Shimadzu LC-10ADVP, :C-10ADVP micro-piston pump, 1 page.

(Continued)

*Primary Examiner* — Nicholas Lucchesi  
*Assistant Examiner* — Jenna Zhang  
(74) *Attorney, Agent, or Firm* — Thorpe North & Western LLP

(57) ABSTRACT

A miniature pump device, with a fluid reservoir that can contain an intravenous drug, hydraulic fluid, or the like. The miniature pump has a motor disposed adjacent the fluid reservoir, and a piston disposed within the fluid reservoir. A power transfer linkage transfers power from the motor to the piston in the fluid reservoir, and a stationary flexible seal is coupled between the fluid reservoir and the power transfer linkage to seal a portion of the power transfer linkage within the fluid reservoir.

24 Claims, 9 Drawing Sheets

OTHER PUBLICATIONS

Archive News Story, "Minature Piston Pump measures 44 x 17.3 x 25.5 mm" and Archive Press Release "New Miniature Postion Pump Great Solution for Low volume Applications", Feb. 12, 2002, 1 page.

E. Clark & Associates, GOTEC, 5 pages.

U.S. Appl. No. 12/604,237, filed Oct. 22, 2009; Stephen C. Jacobsen; office action dated Nov. 15, 2012.

* cited by examiner

MINIATURE PUMP DEVICE AND METHOD

This application claims the benefit of U.S. Provisional Application Ser. No. 60/923,334, filed Apr. 12, 2007, and entitled, "Miniature Pump Device and Method," which is incorporated by reference in its entirety herein.

BACKGROUND OF THE INVENTION

1. Field of the Invention

The present invention relates generally to fluid pumps, and more particularly to miniature jack or piston pumps.

2. Related Art

Miniature pumps have been used in a variety of applications such as drug delivery devices, miniature hydraulic systems, and the like. Some miniature pumps flex a diaphragm or use a dragging seal to create a vacuum to move fluid into and out of the pump. Other miniature pumps, such as piston pumps, have to rotate or slide a seal in order to push or impel fluid through the pump. The moving seals in these types of pumps have presented problems in that relatively significant amounts of power are needed in order to overcome resistive frictional forces and move the seals. Consequently, relatively large batteries or other power sources have been required to power these miniature pumps, thereby reducing the size benefit of the miniature pump.

Additionally, very small pumps typically operate at relatively high frequencies. The rapid cycling of pistons, impellors, and seals can wear the seals and cause leakage of the pumped fluid out of the pump. Moreover, high frequency cycling can cause cavitation, or the generation of gas bubbles, within the fluid flow path in the pump. Bubbles in the fluid stream affect the output volume of the pump and affect pump efficiency. Bubbles can also be dangerous to patients when such pumps are used as drug delivery devices.

SUMMARY OF THE INVENTION

It has been recognized that it would be advantageous to develop a miniature pump device and method for pumping fluid. It has also been recognized that it would be advantageous to develop a miniature pump that has a stationary flexible seal that seals the moving parts of the pump within the fluid reservoir in order to minimize the power consumption of the pump during use, and prevent leakage. It has also been recognized that it would be advantageous to develop a miniature pump that reduces bubble formation in the fluid flow path to minimize turbulence and cavitation in the pumped fluid in order to maximize the flow rate from the pump.

In one aspect, the present invention provides for a miniature pump device including a fluid reservoir and a motor disposed adjacent the fluid reservoir. A piston can be disposed within the fluid reservoir to draw and expel fluid from the fluid reservoir. A power transfer linkage can be coupled between the piston and the motor and can transfer power from the motor to the piston in the fluid reservoir. The power transfer linkage can be at least partially disposed in the fluid reservoir. A stationary flexible seal is coupled between the fluid reservoir and the power transfer linkage to seal a portion of the power transfer linkage within the fluid reservoir and restrict fluid from escaping from fluid reservoir as the power transfer linkage moves during use.

In a more detailed aspect of the invention, the piston of the pump can include a hollow cylinder with a fluid chamber forming a fluid flow path between an inlet in fluid communication with the fluid reservoir and an outlet. A rod can be slidably disposed in the hollow cylinder between an open position and a closed position. The rod can be sized and shaped to have a near interference fit with the hollow cylinder, and can turbulently draw fluid from the fluid reservoir into the fluid chamber of the cylinder through the inlet when the rod is in the open position. The turbulence of the fluid entering the chamber can displace any gaseous bubbles within the chamber. The rod can expel the contents of the fluid chamber through the outlet by sliding the rod to the closed position.

The present invention also provides for a method for expelling gas bubbles from a miniature pump device including providing a miniature pump having a piston disposed in a fluid reservoir. The piston can have a hollow cylinder and a rod slidably disposed in the hollow cylinder. The rod can be sized and shaped to have a near interference fit within the hollow cylinder. The rod can be slid within the hollow cylinder past an inlet to an open position to turbulently draw fluid from the fluid reservoir through the inlet and into a chamber within the hollow cylinder. The turbulence of the fluid entering the chamber can displace any gaseous bubbles within the chamber. The rod can be slid to a closed position with the rod closing the inlet and pushing the contents of the chamber through an outlet of the hollow cylinder.

Additional features and advantages of the invention will be apparent from the detailed description which follows, taken in conjunction with the accompanying drawings, which together illustrate, by way of example, features of the invention.

DETAILED DESCRIPTION

Figure 1:
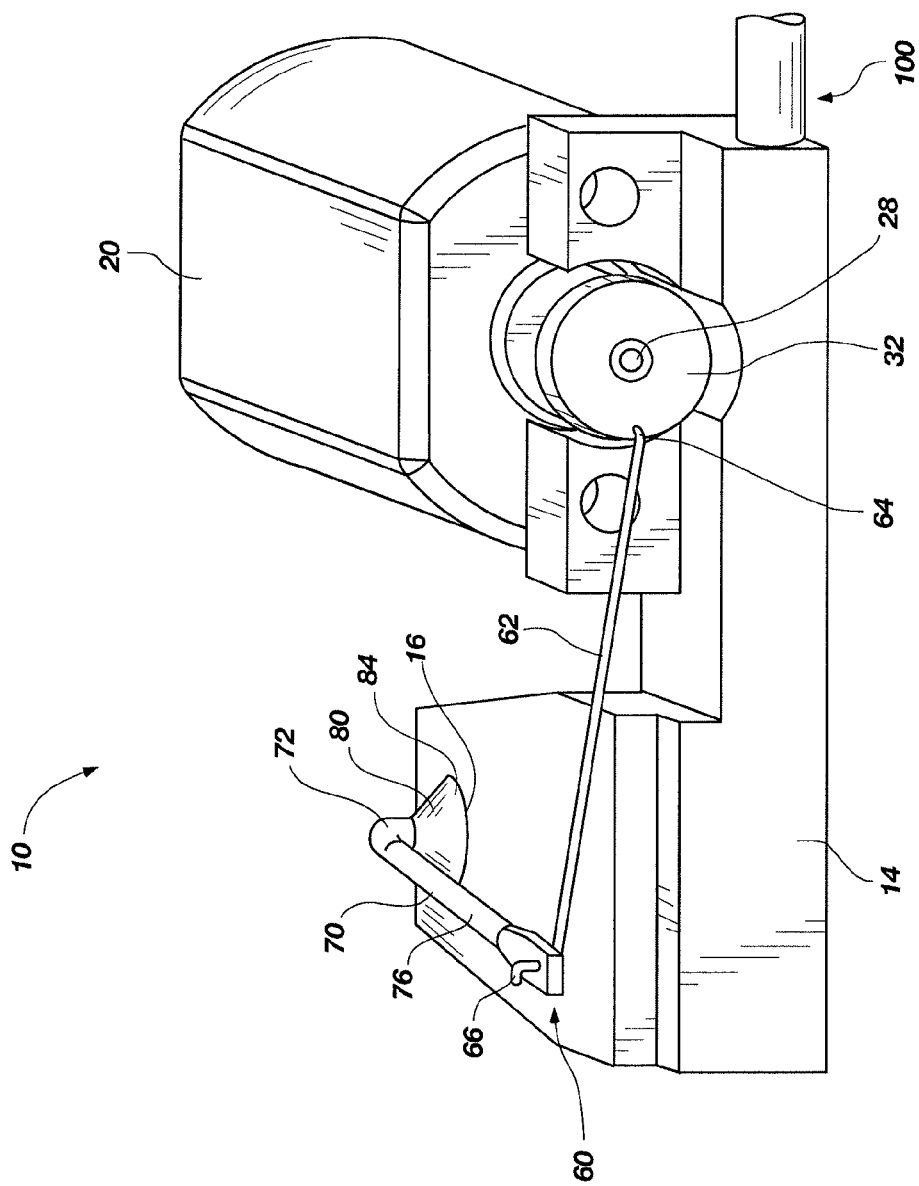
FIG. 1 is a perspective view of a miniature pump device in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention generally provides for a miniature pump that can be used as a drug delivery device, a miniature hydraulic pump, or the like. The pump has a stationary flexible seal to seal the moving parts of the pump within the fluid reservoir. The pump has a motor outside the fluid reservoir that drives a piston inside the fluid reservoir. A power transfer linkage extends from the motor to the piston and transfers power from the motor to the piston. The stationary flexible seal surrounds a portion of the power transfer linkage and seals against the fluid reservoir to restrict fluid leakage from the reservoir as the power transfer linkage moves. The flexible seal is bonded to the power transfer linkage and flexes around the power transfer linkage during use to maintain the seal around the power transfer linkage. The piston is also configured to restrict the formation of bubbles within the fluid flow path of the pump.

As illustrated in FIGS. 1-4, a miniature pump device, shown generally at 10, is shown in accordance with an embodiment of the present invention. The miniature pump 10 can have a fluid reservoir 14 that can contain an intravenous drug, hydraulic fluid, or the like. The pump 10 can also have a motor 20 disposed adjacent the fluid reservoir 14, and a piston, shown generally at 100, disposed within the fluid reservoir 14. A power transfer linkage, shown generally at 60, can transfer power from the motor 20 to the piston 100 in the fluid reservoir 14, and a stationary flexible seal 80 can be coupled between the fluid reservoir 14 and the power transfer linkage 60 to seal a portion of the power transfer linkage 60 within the fluid reservoir 14. Thus, fluid leakage can be restricted by the flexible seal as the motor 20 drives the power transfer linkage 60.

The motor 20 can be a small electrical motor, as known in the art, and a power source 24 (FIG. 4), such as a battery, can be electrically couplable to the motor 20. It will be appreciated that an AC or DC motor, or combination thereof, can be used to power the miniature pump 10 along with common transformers, as known in the art. The motor 20 can have an output shaft 28 that can rotate a drive wheel 32. The drive wheel 32 can output power from the motor 20 in the form of rotational energy.

A controller 36 can be electrically coupled between the power source 24 and the motor 20 to control actuation of the motor 20, and hence operation of the miniature pump 10. It will be appreciated the controller 36 can include a programmable electronic switch that can precisely control the flow from the pump 10. Additionally, the controller 36 can be a simple on/off switch that can be activated by a user or other activation source.

The power transfer linkage 60 can include a flexible rod 62 that can translate rotational energy from the drive wheel 32 of the motor 20 into linear energy to power the linear movement of the piston 100. The flexible rod 62 can have a drive wheel end 64 and a power transfer end 66. The drive wheel end 64 can be pivotally coupled to the drive wheel 32 so that as the drive wheel rotates, the drive wheel end 64 of the flexible rod 62 moves in a circular motion which in turn moves the power transfer end 66 back and forth in a substantially linear motion. The flexible rod 62 can be a thin elastically flexible wire rod that can flex under an applied load from the drive wheel 32 and return to an original shape when no load is applied. Advantageously, the flexible rod 62 eliminates the need for a complex joint between the drive wheel 32 and the U-shaped linkage 70.

A U-shaped linkage 70 can be pivotally coupled to the power transfer end 66 of the flexible rod. The U-shaped linkage can have a reservoir arm 74, and an outside arm 76 that extend from a base 72 to form a U-shaped linkage 70. The reservoir arm 74 can be at least partially enclosed within the fluid reservoir 14. The outside arm 76 can be outside the fluid reservoir 14.

The U-shaped linkage 70 can be mounted to the fluid reservoir 14 such that the U-shaped linkage 70 can pivot about the base 72, and can be oriented in a substantially transverse relationship to the flexible rod 62. The outside arm 76 of the U-shaped linkage 70 can be pivotally coupled to the power transfer end 66 of the flexible rod 60 so that as the power transfer end 66 of the flexible rod 62 moves back and forth, the outside arm 76 is also moved back and for the and pivots the U-shaped linkage 70. The reservoir arm 74 can be pivotally coupled to the piston 100 so that as the U-shaped linkage 72 is pivoted back and forth, the reservoir arm 74 moves the piston 100 back and forth.

In one aspect the motor 20 can cycle the power transfer linkage at a frequency greater than 100 Hz. In another aspect, the motor can cycle the power transfer linkage approximately 200 Hz. In this way, the power transfer linkage 60 can translate rotary energy or power from the motor 20 to linear power to drive the piston 100. Thus, the power transfer linkage 60 is an example of one means for transferring power to provide power from the motor 20 to the piston 100 to pump fluid from the fluid reservoir 14.

The flexible seal 80 can be coupled between the fluid reservoir 14 and the power transfer linkage 60. The flexible seal 80 can seal a portion of the power transfer linkage 60 in the fluid reservoir 14 and restrict fluid from escaping from fluid reservoir 14 as the power transfer linkage 60 moves during use. The flexible seal 80 can be an elastomeric plug 84 disposed in a wall 16 of the fluid reservoir 14 with a portion of the power transfer linkage 60 extending through the elastomeric plug 84. The elastomeric plug 84 can be bonded to the power transfer linkage 60 to form a seal on the power transfer linkage 60. The elastomeric plug 84 can elastically flex as the power transfer linkage 60 moves during use. Thus, in one aspect the motor can cycle the power transfer linkage at a frequency greater than 100 Hz and the power transfer linkage can flex the flexible seal at a frequency greater than 100 Hz. In another aspect, the power transfer linkage flexes the flexible seal at a frequency of approximately 200 Hz.

Figure 2:
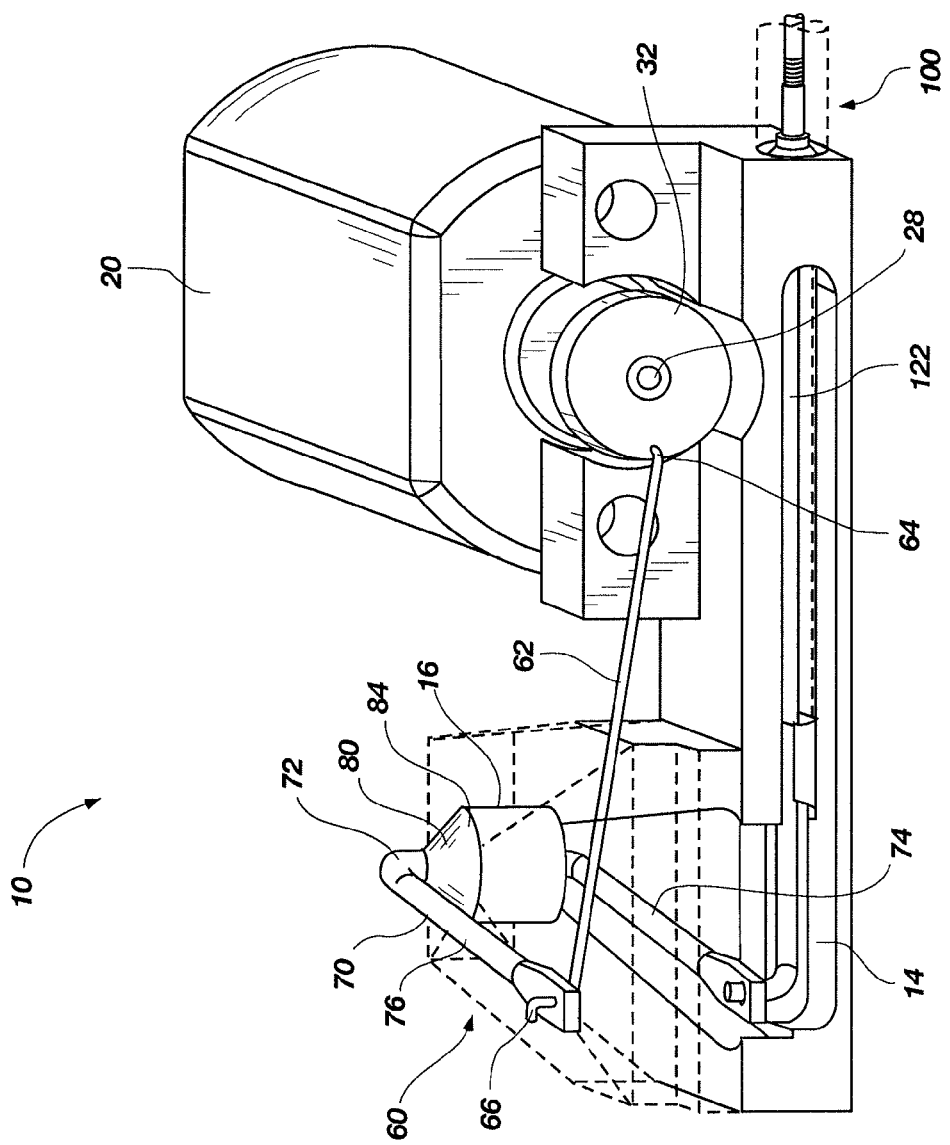
FIG. 2 is a schematic view of the miniature pump device of FIG. 1, showing an internal view of a fluid reservoir.
Figure 3:
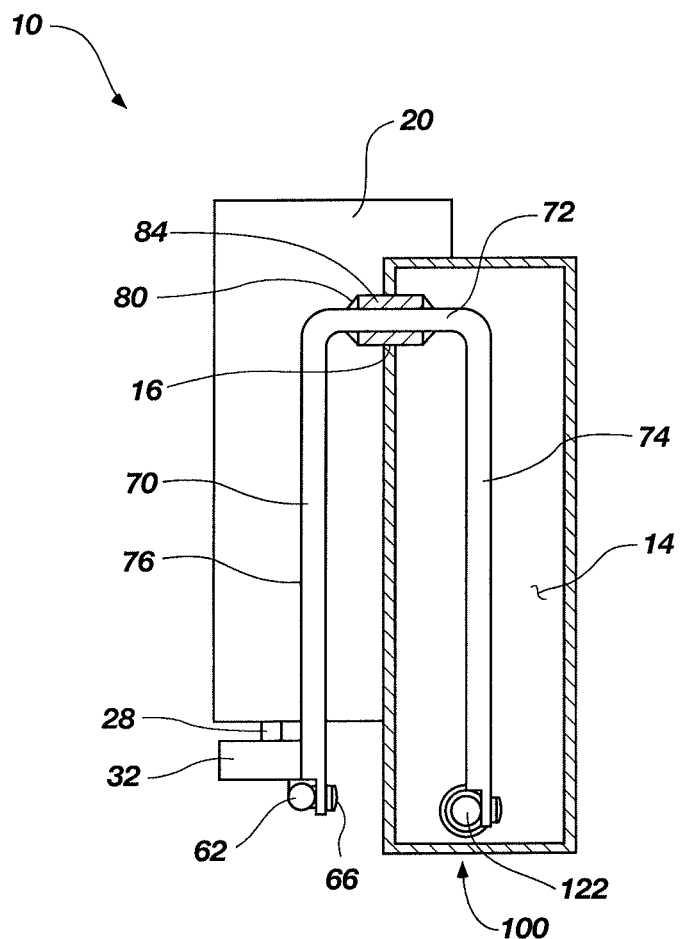
FIG. 3 is cross section view of the miniature pump device of FIG. 1.
Figure 4:
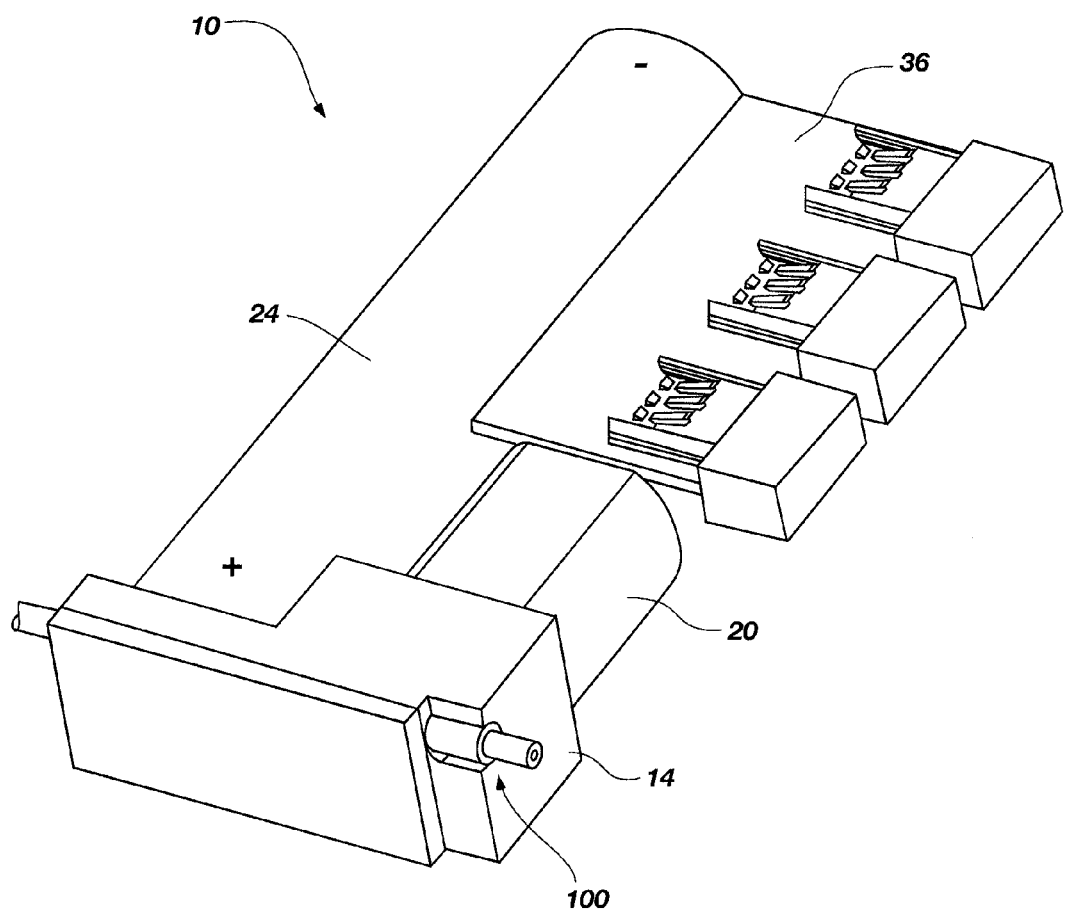
FIG. 4 is a perspective view of the miniature pump device of FIG. 1, shown with a power source and a controller.

As shown in FIGS. 1-3, the elastomeric plug 84 of the flexible seal 80 can be bonded to the base 72 of the U-shaped linkage 70 so that the outside arm 76 is outside the fluid reservoir 14 and the reservoir arm 74 is inside the fluid reservoir 14. The elastomeric plug 84 and U-shaped linkage 70 can be placed in an aperture 18 in the fluid reservoir 14, and the elastomeric plug 84 can seal against the reservoir arm 74 inside the fluid reservoir 14.

In use, the elastomeric plug 84 can rotationally stretch or flex with the base 72 of the U-shaped linkage 70 as the U-shaped linkage 70 pivots about the base 72 without breaking the seal around the base 72 or the fluid reservoir 14. Additionally, the elastomeric plug 84 can stretch or flex elastically so that the plug 84 can return to an un-flexed position when not in use. Advantageously, stretching and flexing the flexible seal 80 instead of sliding or moving a seal requires less energy to actuate the piston 100 and, thus, the pump 10 can employ a smaller power source 24 in order to pump fluid. Thus, the flexible seal 80, including the elastomeric plug 84, is an example of one means for flexibly sealing a portion of the power transfer linkage 60 in the fluid reservoir 14 to restrict fluid from escaping from fluid reservoir 14 as the power transfer linkage 60 moves during use.

Figure 5:
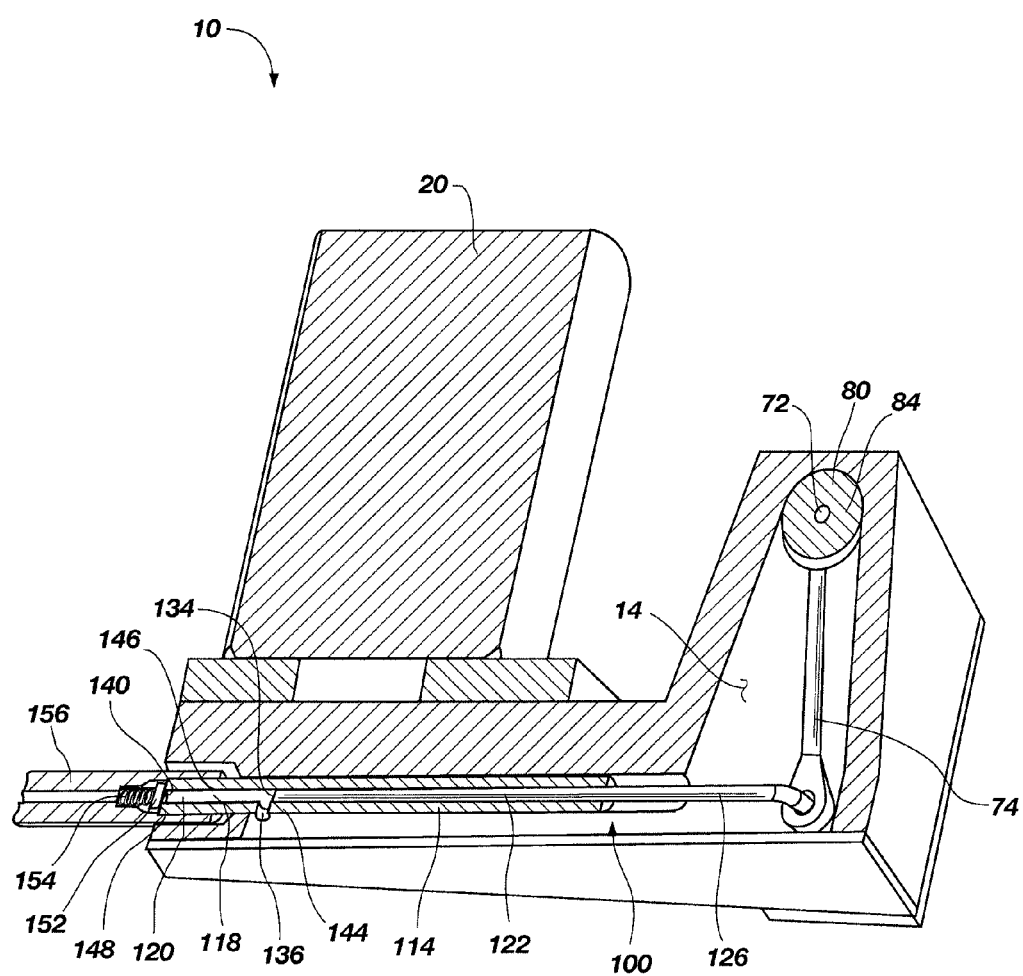
FIG. 5 is a perspective cut-away view of the miniature pump device of FIG. 1, shown with a piston in an open position.
Figure 6:
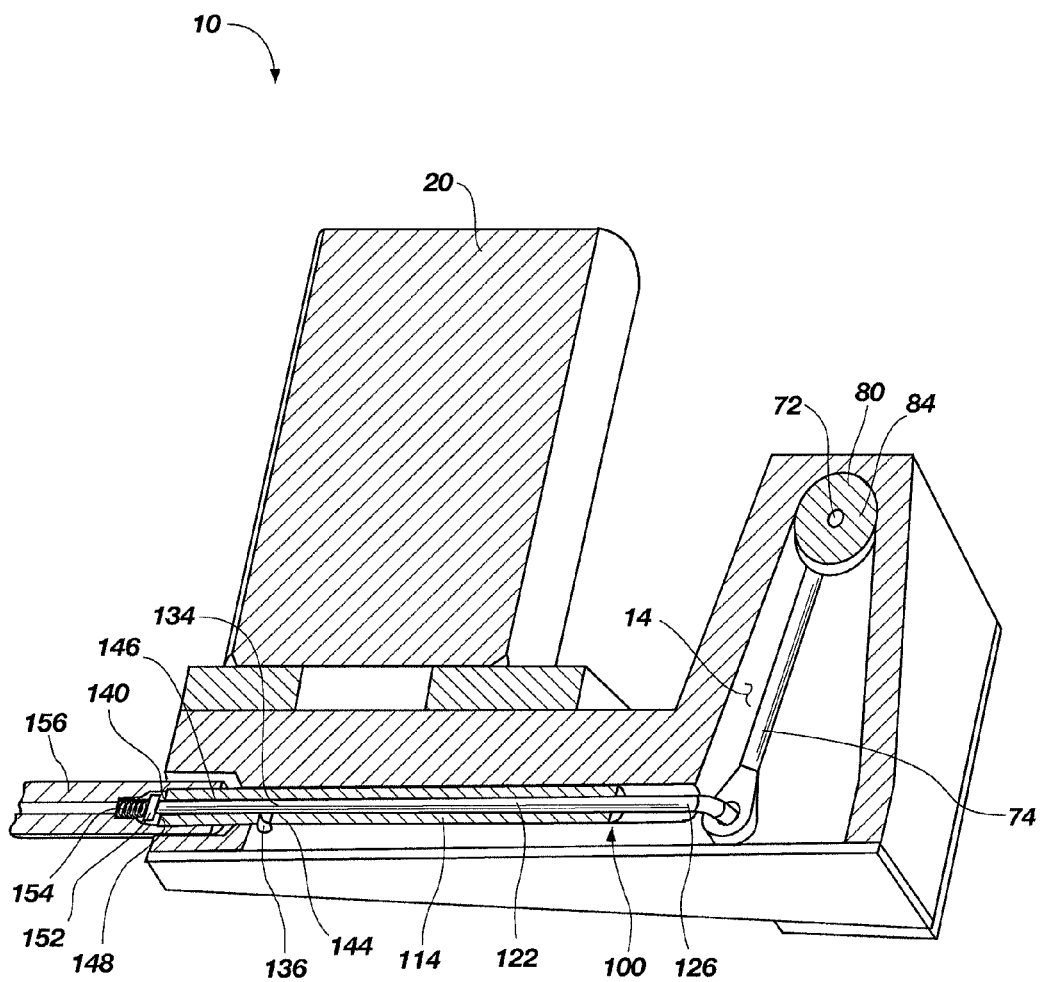
FIG. 6 is a perspective cut-away view of the miniature pump device of FIG. 5, shown with the piston in a closed position.

Referring to FIGS. 5-6, a cut away view of the miniature pump 10 is shown to better illustrate the piston 100. The piston 100 can be entirely disposed in the fluid reservoir 14, and can draw fluid from the fluid reservoir 14 and expel the drawn fluid from the fluid reservoir 14. The piston can have a hollow cylinder 114 that has a fluid chamber 118 forming a fluid flow path 120 between an inlet 136 that is in fluid communication with the fluid reservoir 14 and an outlet 140 in the top 148 of the hollow cylinder 114.

A piston rod 122 can be slidably disposed in the hollow cylinder 114, and can be slidable between an open position, as shown in FIG. 5, and a closed position, as shown in FIG. 6. The piston rod 122 can be sized and shaped to have a near interference fit with the fluid chamber 118 of the hollow cylinder 114. The piston rod 122 can extend from within the chamber 118 to an end 126 in the fluid reservoir 14. The end in the fluid reservoir 14 can be pivotally coupled to the reservoir arm 74 of the U-shaped linkage 70 so that as the reservoir arm 74 moves back and forth, the piston rod 122 is moved between the open and closed positions. In one aspect, movement of the piston rod 122 to the open position can create a vacuum in the chamber 118, and the vacuum can draw fluid from the fluid reservoir 14 into the chamber 118.

The piston rod 122 can be precisely sized to form a slidable fluidic seal with the chamber 118 so that fluid cannot escape the chamber 118 by moving past the piston rod 122. The piston rod 122 can also have substantially flat face 134 that can be substantially orthogonal to the side wall 146 of the chamber 118. It will be appreciated that the substantially orthogonal interface between the flat face of the piston rod 122 and the chamber 118 can reduce stagnation and cavitation of the fluid as it enters and moves through the chamber 118. Specifically, the flat face 134 can push the entire volume of the chamber 118 as the piston rod 122 moves during use.

The fluid inlet 136 can be a hole or aperture in a side wall 144 of the cylinder 114 that extends through the side wall 144 to the chamber 118. The outlet 140 can be a hole at the top 148 of the cylinder 114. The cylinder 114 can be disposed in the fluid reservoir 14 so that when the piston rod 122 is in the open position, fluid from the fluid reservoir 14 can flow into the chamber 118 through the inlet 136.

A valve 152 can be disposed across the top 148 of the cylinder 114 and can be biased to close off the top 148 of the cylinder 114. In one aspect, the valve 152 can be biased by a spring 154 to maintain the valve 152 in a closed position. In another aspect, backflow pressure from fluid in an outlet fluid line 156 can bias the valve 152 to a closed position. The valve 152 can be opened by force from within the chamber 118. The top 148 of the cylinder 114 can be coupled to the outlet fluid line 156. The outlet fluid line 156 can deliver the fluid to a desired location. The valve 152 can be entirely disposed within the outlet fluid line 156. In one aspect, the valve 152 can be a gate valve, as shown in FIGS. 5-6. In another aspect, the valve can be a ball valve. It will be appreciated that any linearly closing valve, as known in the art, can be used to close the chamber 118.

In use, the piston 100 can turbulently draw fluid from the fluid reservoir 14 into the fluid chamber 118 of the cylinder 114 through the inlet 136 when the rod 122 is in the open position. Advantageously, the turbulence of the fluid entering the chamber 118 can displace any gaseous bubbles within the chamber 118. The piston rod 122 can then expel the contents of the fluid chamber 118 through the outlet 140 by sliding the piston rod 122 to the closed position. Sliding the piston rod 122 to the closed position pushes the fluid contained within the chamber 118 toward the outlet 140 and the valve 152. The fluid being pushed by the piston rod 122 can force the valve open so the fluid can leave the chamber 118 and enter the outlet fluid line 156. In the closed position the piston rod 122 can contact and force open the valve 152 so that the entire volume of the chamber 118 can be filled with the piston rod 122 thereby leaving no empty space in the chamber 118 in which stagnant bubbles can remain. Thus, the piston rod 122 and the hollow cylinder 114 together can form a piston 100 that can expel gas bubbles from the fluid chamber 118 of the hollow cylinder 114. A piston 100, including a flat face piston rod 122 slidably disposed within a hollow cylinder 114, is an example of one means for expelling gas bubbles from the piston 100.

In one aspect, the piston rod 122 and the cylinder 114 can be made from a glass material in order to provide a low friction interface between the piston rod 122 and the chamber 118 in the cylinder 114. Advantageously, the low friction interface between the piston rod 122 and the chamber 118 requires only small amounts of energy to move the piston rod 122 in the chamber 118. Thus, the pump 10 of the present invention only needs a small power source 24 to actuate the piston 100.

The design of the piston 100 provides several advantages to the miniature pump 10. For example, as noted above, the flat face 134 and precision fit of the piston rod 122 against the cylinder 114 operate to push the entire volume of the chamber 118 out of the chamber 118 when the piston 100 moves during use. It will be appreciated that bubbles can form from cavitation or turbulence of fluid flow into and out of the chamber 118. Moreover, bubbles can become stuck in the chamber 118 by wicking or other capillary forces. These stagnant bubbles can fill a portion of the volume of the chamber 118 and therefore decrease the output volume of the pump 10. Advantageously, the flat face 134 and precision fit of the piston rod 122 forces a complete evacuation of the contents of the chamber 118, thereby leaving no space within the chamber 118 for bubbles to remain. Hence, the design of piston 100 in the pump 10 of the present invention can maximize the flow rate of the pump 10.

Additionally, it is a particular advantage of the miniature pump 10 of the present invention that a small power source 24 can be used to power the motor 20 and the piston 100. It will be appreciated that a large power source or battery makes placement of a pump in small and confined spaces extremely difficult, if not impossible in many cases. For example, a miniature pump used as sub-dermal drug delivery device cannot be disposed below the skin in the abdominal cavity of a patient if the pump requires a battery larger than the space within the abdominal cavity in order to operate. Furthermore, multiple batteries and their eventual replacement can be a complex task in the small spaces such a miniature pump is likely to be used. Consequently, the stationary flexible seal 80 and the low friction interface of the piston 100 allow the miniature pump 10 of the present invention to operate with much smaller power sources than other pumps of similar volumetric output. Thus, in one aspect, the miniature pump device 10 of the present invention requires only approximately ¼ the power needed by other pumps of similar volumetric output, and can be powered by a single AAA size battery.

Figure 7:
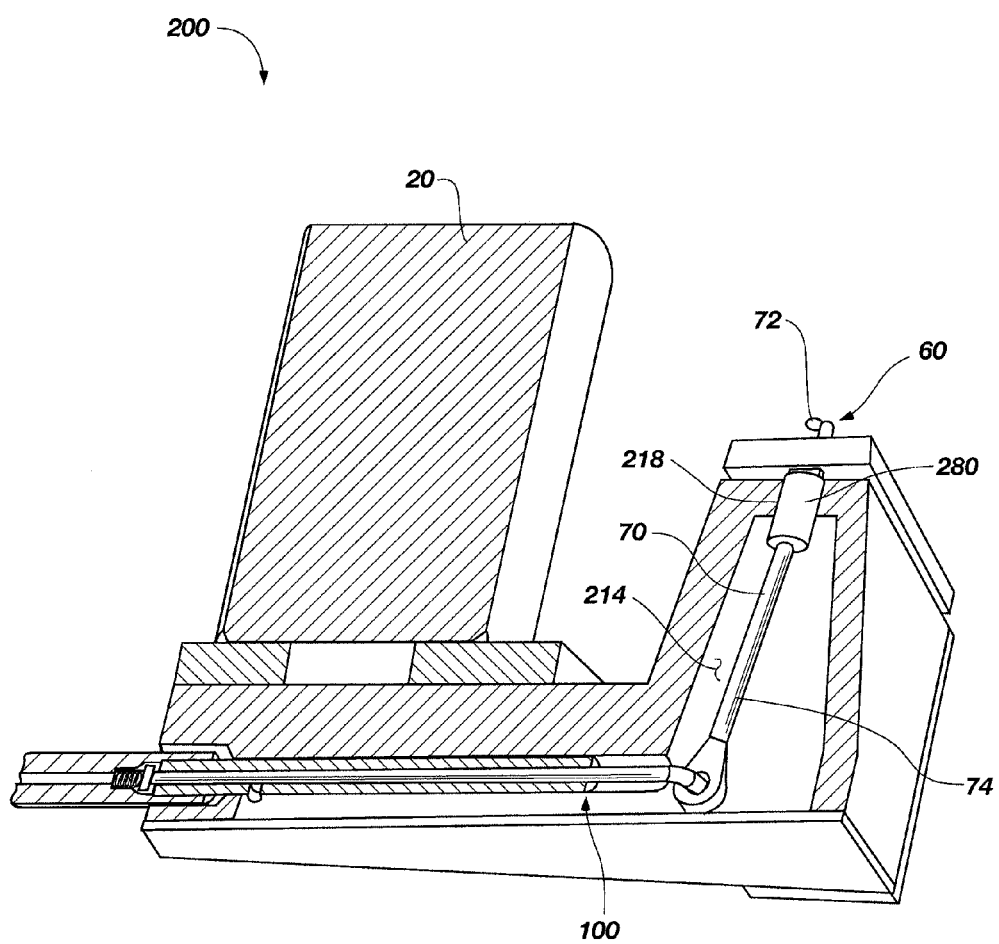
FIG. 7 is a perspective cut-away view of a miniature pump device in accordance with another embodiment of the present invention, shown with a piston in a closed position.
Figure 8:
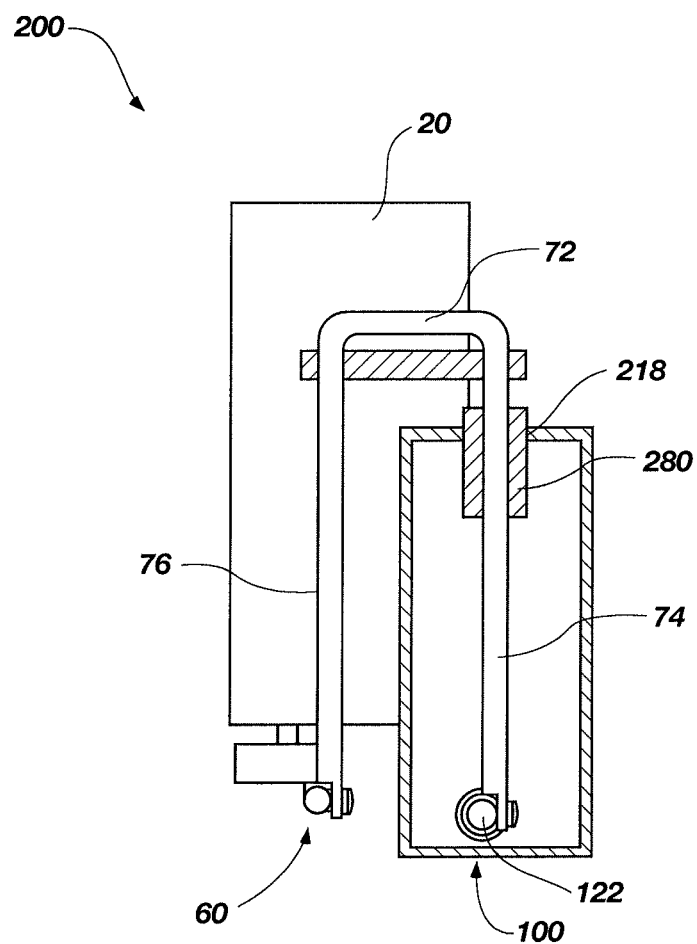
FIG. 8 is a cross sectional view of the miniature pump of FIG. 7.

As illustrated in FIGS. 7-8, a miniature pump device, shown generally at 200, is shown in accordance with another embodiment of the present invention. The miniature pump 200 is similar in many respects to the miniature pump device 10 described above. The miniature pump device 200 can have a fluid reservoir 214 that can contain an intravenous drug, hydraulic fluid, or the like. The pump 200 can also have a motor 20 disposed adjacent the fluid reservoir 214, and a piston 100 disposed within the fluid reservoir 214. A power transfer linkage, shown generally at 60, can transfer power from the motor 20 to the piston 100 in the fluid reservoir 214, and a stationary flexible seal 280 can be coupled between the fluid reservoir 214 and the power transfer linkage 60 to seal a portion of the power transfer linkage 60 within the fluid reservoir 214. Thus, fluid leakage can be restricted by the flexible seal 280 as the motor 20 drives the power transfer linkage 60.

The power transfer linkage 60 can include a U-shaped linkage 70 that can have an outside arm 76, a base 72, and a reservoir arm 74. The reservoir arm 74 can extend at least partially into the fluid reservoir 214. The flexible seal 280 can be bonded to the reservoir arm 74 and can fit within an aperture 218 in the fluid reservoir 214. The flexible seal 280 can seal around the aperture 218 in the fluid reservoir 214 to restrict fluid leakage from the reservoir 214. The flexible seal 280 can elastically flex as the reservoir arm 74 of the U-shaped linkage 70 moves in the aperture 218. It will be appreciated that the flexible seal 280 flexes linearly away from or toward the reservoir arm 74, as opposed to the rotational flexing of the flexible seal 80 that is bonded to the base 72 of the U-shaped linkage 60, shown in FIGS. 1-6, and described above.

Figure 9:
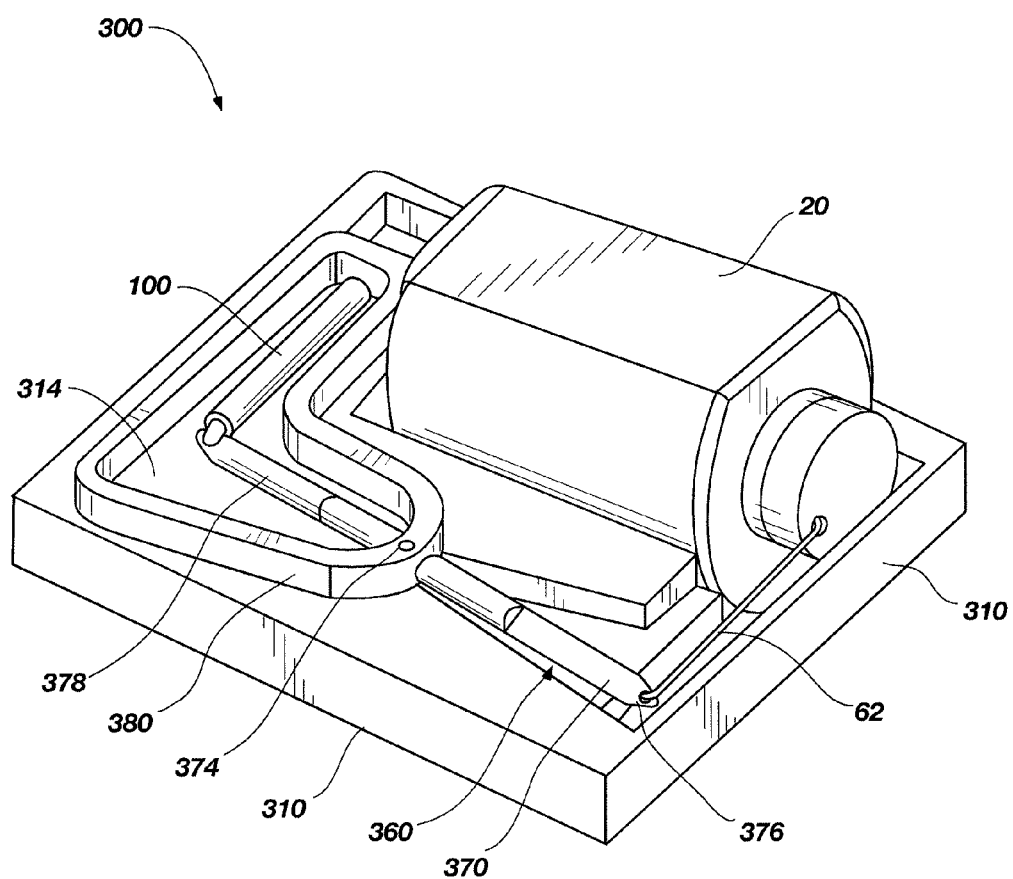
FIG. 9 is a perspective view of a miniature pump device in accordance with another exemplary embodiment of the present invention.

Illustrated in FIG. 9, a miniature pump device, shown generally at 300, is shown in accordance with another embodiment of the present invention. The miniature pump 300 is similar in many respects to the miniature pump device 10 described above. The miniature pump device 300 can have a fluid reservoir 314 that can contain an intravenous drug, hydraulic fluid, or the like. The pump 300 can also have a motor 20 disposed adjacent the fluid reservoir 314, and a piston 100 disposed within the fluid reservoir 314. A power transfer linkage, shown generally at 360, can transfer power from the motor 20 to the piston 100 in the fluid reservoir 314, and a stationary flexible seal 380 can be coupled between the fluid reservoir 314 and the power transfer linkage 360 to seal a portion of the power transfer linkage 360 within the fluid reservoir 314. Thus, fluid leakage can be restricted by the flexible seal 380 as the motor 20 drives the power transfer linkage 360.

The power transfer linkage 360 can include a flexible linkage 62 coupled to an end 376 of a linear rocker arm 370. The linear rocker arm 370 can extend at least partially into the fluid reservoir 314. The linear rocker arm 370 can be pinned to a pump housing 310 by a pivot pin 374. The linear rocker arm 370 can pivot or rock about the pivot pin 374. An opposite end 378 of the linear rocker arm can be coupled to the piston 100. Thus, in use, the motor can move the flexible linkage 62 which can pivot the linear rocker arm 370 about the pivot pin 374, thereby moving the piston to pump fluid from the fluid reservoir 314.

The flexible seal 380 can be bonded to the linear rocker arm 370 and can extend from the linear rocker arm entirely around a circumference of the fluid reservoir 214. In this way the flexible seal can seal around the linear rocker arm 370 and also around the entire fluid reservoir 314 to restrict fluid leakage from the reservoir 314. The flexible seal 380 can elastically flex as the linear rocker arm 370 rocks about the pivot pin 374. It will be appreciated that a portion of the flexible seal 380 on one side of the rocker arm 370 and a portion compresses on an opposite side of the rocker arm, as opposed to the rotational or linear flexing of the flexible seals shown in FIGS. 1-8, and described above.

The present invention also provides for a method for expelling gas bubbles from a miniature pump device including providing a miniature pump having a piston disposed in a fluid reservoir. The piston can have a hollow cylinder and a rod slidably disposed in the hollow cylinder. The rod can be sized and shaped to have a near interference fit within the hollow cylinder. The rod can be slid within the hollow cylinder past an inlet to an open position to turbulently draw fluid from the fluid reservoir through the inlet and into a chamber within the hollow cylinder. The turbulence of the fluid entering the chamber can displace any gaseous bubbles within the chamber. The rod can be slid to a closed position with the rod closing the inlet and pushing the contents of the chamber through an outlet of the hollow cylinder.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. A miniature pump device, comprising:
   a) a fluid reservoir;
   b) a motor, configured to electrically couple to a power source, and disposed adjacent the fluid reservoir;
   c) a piston, disposed in the fluid reservoir, and configured to draw and expel fluid from the fluid reservoir;
   d) a power transfer linkage coupled between the piston and the motor, said power transfer linkage having a pivoting member with a pivoting portion at least partially disposed in the fluid reservoir; and
   e) a flexible seal disposed circumferentially about the pivoting member, that seals the fluid reservoir and restricts fluid from escaping from the fluid reservoir as the power transfer linkage moves during use.

2. A device in accordance with claim 1, wherein the flexible seal further comprises:
   an elastomeric plug, disposed through a wall of the fluid reservoir with a portion of the pivoting member extending through the elastomeric plug; and
   the elastomeric plug being bonded to the pivoting member to form a seal thereon, and configured to elastically flex as the power transfer linkage moves during use.

3. A device in accordance with claim 2, wherein the elastomeric plug linearly flexes as the pivoting member pivots during use.

4. A device in accordance with claim 1, wherein the power transfer linkage further comprises:
   a flexible rod configured to translate rotational energy from the motor into linear energy; and
   said pivoting member, which comprises a U-shaped linkage configured to receive linear energy from the flexible rod and transfer the linear energy to the piston.

5. A device in accordance with claim 4, wherein the flexible seal further comprises:
   an elastomeric plug, disposed in a wall of the fluid reservoir and bonded to a base of the U-shaped linkage to form a seal thereon that rotationally flexes as the base of the U-shaped linkage pivots during use.

6. A device in accordance with claim 1, wherein the piston further comprises:
   a) a hollow cylinder, having a fluid chamber forming a fluid flow path between an inlet in fluid communication with the fluid reservoir and an outlet; and
   b) a rod, slidably disposed in the hollow cylinder between an open position and a closed position, the rod being sized and shaped to have a near interference fit with the hollow cylinder, and configured to turbulently draw fluid from the fluid reservoir into the fluid chamber of the cylinder through the inlet when the rod is in the open position, the turbulence of the fluid entering the chamber displacing any gaseous bubbles within the chamber, and to expel contents of the fluid chamber through the outlet by sliding the rod to the closed position, the rod configured to expel gas bubbles from the fluid chamber of the hollow cylinder.

7. A device in accordance with claim 1, wherein the power transfer linkage flexes the flexible seal at a frequency greater than 100 Hz.

8. A device in accordance with claim 1, wherein the power source includes a battery disposed adjacent the motor.

9. A device in accordance with claim 1, further comprising:
a controller, disposed adjacent the motor, configured to activate the motor to control the output of the miniature pump.

10. A miniature pump device, comprising:
a) a fluid reservoir;
b) a motor, disposed adjacent the fluid reservoir and electrically couplable to a power source;
c) a power transfer linkage coupled between a piston and the motor, said power transfer linkage having a pivoting member with a pivoting portion at least partially disposed in the fluid reservoir;
d) a flexible seal disposed circumferentially about the pivoting member, that seals the fluid reservoir and restricts fluid from escaping from the fluid reservoir as the power transfer linkage moves during use; and
e) the piston, disposed in the fluid reservoir and operably coupled to the power transfer linkage to receive linear power from the power transfer linkage, further comprising:
i) a hollow cylinder, having a fluid chamber forming a fluid flow path between an inlet that is in fluid communication with the fluid reservoir and an outlet; and
ii) a rod, slidably disposed in the hollow cylinder between an open position and a closed position, the rod being sized and shaped to have a near interference fit with the hollow cylinder, and configured to turbulently draw fluid from the fluid reservoir into the fluid chamber of the cylinder through the inlet when the rod is in the open position, the turbulence of the fluid entering the chamber displacing any gaseous bubbles within the chamber, and to expel contents of the fluid chamber through the outlet by sliding the rod to the closed position, the rod configured to expel gas bubbles from the fluid chamber of the hollow cylinder.

11. A device in accordance with claim 10, wherein the piston further comprises:
a valve, associated with the outlet, and engageable by the rod to open the valve when the rod is in the closed position.

12. A device in accordance with claim 10, wherein the flexible seal further comprises:
an elastomeric plug, disposed through a wall of the fluid reservoir with a portion of the pivoting member extending through the elastomeric plug; and
the elastomeric plug being bonded to the pivoting member to form a seal thereon, and configured to elastically flex as the power transfer linkage moves during use.

13. A device in accordance with claim 10, wherein the power transfer linkage further comprises:
a flexible rod configured to translate rotational energy from the motor into linear energy, and to transfer the linear energy to the piston; and
said pivoting member, which comprises a U-shaped linkage configured to receive linear energy from the flexible rod and transfer the linear energy to the piston.

14. A device in accordance with claim 13, wherein the flexible seal further comprises:
an elastomeric plug, disposed in a wall of the fluid reservoir with a base of the U-shaped linkage extending through elastomeric plug; and
the elastomeric plug being bonded to the base of the U-shaped linkage to form a seal thereon that rotationally flexes as the base of the U-shaped linkage pivots during use.

15. A device in accordance with claim 10, wherein the power transfer linkage flexes the flexible seal at a frequency greater than 100 Hz.

16. A device in accordance with claim 10, wherein the power source includes a battery disposed adjacent the motor.

17. A device in accordance with claim 10, further comprising:
a controller, disposed adjacent the motor, configured to activate the motor to control the output of the miniature pump.

18. A miniature pump device, comprising:
a) a fluid reservoir;
b) a motor, electrically couplable to a power source, and disposed adjacent the fluid reservoir;
c) a piston, disposed in the fluid reservoir, and configured to draw and expel fluid from the fluid reservoir;
d) means for transferring power coupled between the piston and the motor, said means for transferring power having a pivoting member with a pivoting portion at least partially disposed in the fluid reservoir; and
e) means for flexibly sealing the fluid reservoir, said means for flexibly sealing being disposed circumferentially about the pivoting member to restrict fluid from escaping from the fluid reservoir as the means for transferring power moves during use.

19. A device in accordance with claim 18, wherein the means for transferring power further comprises:
a flexible rod configured to translate rotational energy from the motor into linear energy and to transfer the linear energy to the piston; and
said pivoting member, which comprises a U-shaped linkage configured to receive linear energy from the flexible rod and transfer the linear energy to the piston.

20. A device in accordance with claim 18, wherein the means for sealing further comprises:
an elastomeric plug, disposed through a wall of the fluid reservoir with a portion of the pivoting member extending through the elastomeric plug; and
the elastomeric plug being bonded to the pivoting member to form a seal thereon, and configured to elastically flex as the means for transferring power moves during use.

21. A device in accordance with claim 18, wherein the piston further comprises:
means for expelling gas bubbles from the piston.

22. A device in accordance with claim 21, wherein the means expelling gas bubbles comprises:
a) a hollow cylinder, having a fluid chamber forming a fluid chamber between an inlet in fluid communication with the fluid reservoir and an outlet; and
b) a rod, slidably disposed in the hollow cylinder between an open position and a closed position, the rod being sized and shaped to have a near interference fit with the hollow cylinder, and configured to turbulently draw fluid from the fluid reservoir into the fluid chamber of the cylinder through the inlet when the rod is in the open position, the turbulence of the fluid entering the chamber displacing any gaseous bubbles within the chamber, and to expel contents of the fluid chamber through the outlet by sliding the rod to the closed position, the rod configured to expel gas bubbles from the fluid chamber of the hollow cylinder.

23. A method for expelling gas bubbles from a miniature pump device, comprising:
   a) providing a miniature pump having a piston disposed in a fluid reservoir, the piston being coupled to a power transfer linkage having a pivoting member with a pivoting portion at least partially disposed in the fluid reservoir, a flexible seal being disposed circumferentially about the pivoting member to seal the fluid reservoir and restrict fluid from escaping from the fluid reservoir as the power transfer linkage moves during use, the piston including a hollow cylinder and a rod slidably disposed in the hollow cylinder, the rod being sized and shaped to have a near interference fit with the hollow cylinder;
   b) sliding the rod in the hollow cylinder past an inlet to an open position to turbulently draw fluid from the fluid reservoir through the inlet and into a chamber within the hollow cylinder, the turbulence of the fluid entering the chamber displacing any gaseous bubbles within the chamber; and
   c) sliding the rod in the hollow cylinder to a closed position with the rod closing the inlet and pushing the contents of the chamber through an outlet of the hollow cylinder.

24. A miniature pump device, comprising:
   a) a housing defining, in part, a fluid reservoir comprising fluid to be pumped;
   b) a motor, configured to electrically couple to a power source, and disposed adjacent the fluid reservoir;
   c) a piston, disposed in the fluid reservoir, and configured to draw the fluid from the fluid reservoir into a fluid chamber through an inlet fluidly coupled to the fluid reservoir, and to expel the fluid from the fluid chamber through an outlet;
   d) a power transfer linkage, coupled between the piston and the motor, said power transfer linkage having a pivoting member with a pivoting portion at least partially disposed in the fluid reservoir; and
   e) a flexible seal disposed circumferentially about the pivoting member, that seals the fluid reservoir and restricts fluid from escaping from the fluid reservoir as the power transfer linkage moves during use.

* * * * *